United States Patent [19]

Aya et al.

[11] 4,402,731
[45] Sep. 6, 1983

[54] HERBICIDALLY ACTIVE NOVEL SUBSTITUTED TETRAHYDROPYRIMIDINONES

[75] Inventors: Masahiro Aya; Junichi Saito; Kazuomi Yasui, all of Tokyo; Kozo Shiokawa, Kanagawa, all of Japan

[73] Assignee: Nihon Tokushu Noyaku Seizo K.K., Tokyo, Japan

[21] Appl. No.: 340,949

[22] Filed: Jan. 20, 1982

[30] Foreign Application Priority Data

Feb. 20, 1981 [JP] Japan .................................. 56-23122

[51] Int. Cl.³ .................... C07D 239/10; A01N 43/54
[52] U.S. Cl. ......................................... 71/92; 544/315; 544/316; 544/318; 424/251
[58] Field of Search ....................... 544/315, 316, 318; 71/92

[56] References Cited

U.S. PATENT DOCUMENTS 3,551,425 12/1970 Peterson ............................. 544/315
3,905,996 9/1975 Perronnet et al. ................... 544/318

OTHER PUBLICATIONS

Chem. Abs., vol. 57:9860(a), 1968.

*Primary Examiner*—Mary C. Lee
*Attorney, Agent, or Firm*—Sprung, Horn, Kramer & Woods

[57] ABSTRACT

A substituted tetrahydropyrimidinone of the formula

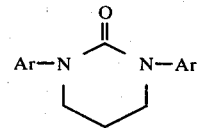

in which
Ar each independently is an α-naphthyl group or a group of the formula,

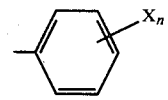

X is halogen, lower alkyl, lower alkoxy, nitro, cyano, lower alkylcarbonyl, lower alkoxycarbonyl, trifluoromethyl or phenoxy, and
n is 0, 1, 2 or 3,
which possesses herbicidal activity.

8 Claims, No Drawings

HERBICIDALLY ACTIVE NOVEL SUBSTITUTED TETRAHYDROPYRIMIDINONES

The present invention relates to certain new substituted tetrahydropyrimidinone derivatives, to a process for their preparation and to their use as herbicides.

The compound 1-methyl-3-phenylhexahydro-2-pyrimidinone is disclosed in Chemical Abstracts, volume 57, 9860a, 1962. However, there has been no disclosure of the use of that compound as a herbicide.

The present invention now provides, as new compounds, the substituted tetrahydropyrimidinone derivatives of the general formula $$\underset{\text{Ar—N}\quad\quad\text{N—Ar}}{\overset{O}{\|}}\quad(I)$$

in which the Ar's may be identical or different and each represents an α-naphthyl group or a group

[structure: phenyl with $X_n$ substituent]

wherein X represents halogen (that is fluorine, chlorine, bromine or iodine), lower alkyl, lower alkoxy, nitro, cyano, lower alkylcarbonyl, lower alkoxycarbonyl, trifluoromethyl or phenoxy, and n represents 0, 1, 2 or 3, the X's being selected independently when n is 2 or 3.

Preferred lower alkyl groups are methyl, ethyl, n- and isopropyl and n-, iso-, sec- or tert-butyl. Preferred lower alkoxy, alkylcarbonyl and alkoxycarbonyl groups are those which contain any of the aforesaid alkyl groups.

The present invention also provides a process for the preparation of a compound of the formula (I) in which (a) a compound of the general formula $$\text{Ar—NH(CH}_2)_3\text{OH} \quad\quad (II),$$

in which Ar has the meaning given above, is reacted with an isocyanate of the general formula $$\text{Ar—N=C=O} \quad\quad (III),$$

in which Ar has the meaning given above and may be identical to or different from the Ar in formula (II), and the product is reacted with a halogenating agent and then with an alkali metal hydroxide, or (b) a compound of the general formula $$\text{Ar—NH(CH}_2)_3\text{Y} \quad\quad (IV),$$

in which
Ar has the meaning given above and
Y represents halogen, is reacted with an isocyanate of the general formula $$\text{Ar—N=C=O} \quad\quad (III),$$

in which Ar has the meaning given above and may be identical to or different from the Ar in formula (IV), and the product is reacted with an alkali metal hydroxide, or (c) a compound of the general formula $$\text{Ar—NH(CH}_2)_3\text{—NH—Ar} \quad\quad (V),$$

in which the Ar's may be identical or different and each have the meaning given above, is reacted with carbonyl chloride or trichloromethyl chloroformate.

It has been found that the compounds of the formula (I) have an excellent herbicidal activity but only a very low toxicity towards warm-blooded animals. In particular, the compounds of this invention have an excellent selective herbicidal activity, which is superior to that of active compounds of similar structure that are described in the literature. The present invention therefore represents an enrichment of the art.

Preferred compounds of the formula (I) are those in which each Ar, independently of the other, represents α-naphthyl or a group

[structure: phenyl with $X_n$ substituent]

wherein X represents fluorine, chlorine, bromine, methyl, isopropyl, methoxy, isopropoxy, nitro, cyano, acetyl, ethoxycarbonyl, trifluoromethyl or phenoxy. Particularly preferred compounds are those wherein at least one Ar represents a phenyl group carrying an X substituent in the 3-position.

If N-3-hydroxpropylaniline, 3,5-dichlorophenyl isocyanate, thionyl chloride and potassium hydroxide are used as reactants in process variant (a), if N-3-chloropropyl-3-trifluoromethylaniline, 2-methoxy-phenyl isocyanate and sodium hydroxide are used as reactants in process variant (b) and if 1-(3-trifluoromethylanilino)-3-anilinopropane and trichloromethyl chloroformate are used as reactants in process variant (c), the course of the reactions may be represented by the following equations:

(a)

[Reaction scheme showing:
Ph—NH(CH$_2$)$_3$OH + 3,5-dichlorophenyl-N=C=O →

Ph—N(—(CH$_2$)$_3$OH)—C(=O)—NH—(3,5-dichlorophenyl) + SOCl$_2$ →

Ph—N(—(CH$_2$)$_3$Cl)—C(=O)—NH—(3,5-dichlorophenyl) + KOH →]

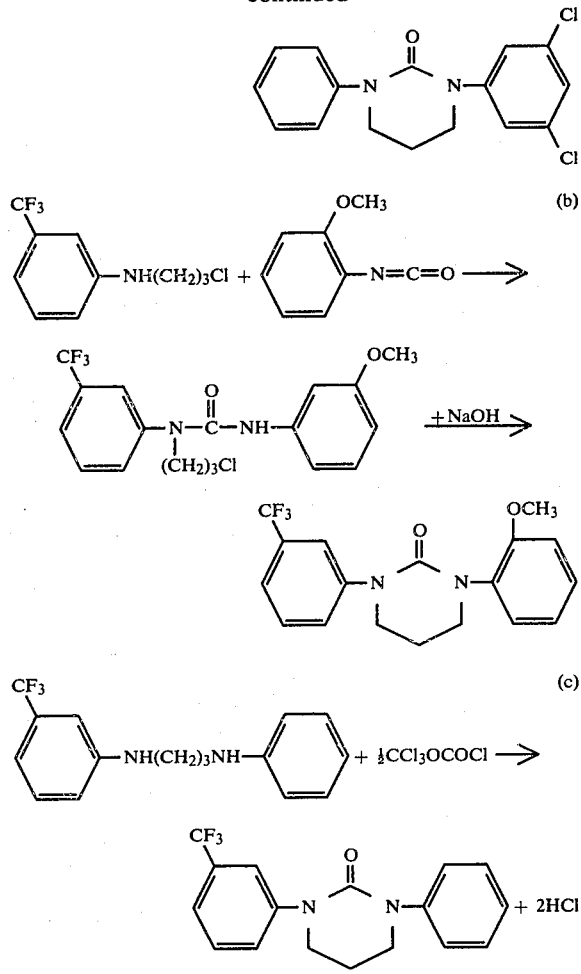

Specific examples of compounds of the general formula (II), which can be used as starting materials in process variant (a), include N-3-hydroxypropyl-3-fluoroaniline, N-3-hydroxypropyl-3-chloroaniline, N-3-hydroxypropyl-3-bromoaniline, N-3-hydroxypropyl-3-toluidine, N-3-hydroxypropyl-3-methoxyaniline, N-3-hydroxypropyl-3-isopropoxyaniline, N-3-hydroxypropyl-3-phenoxyaniline, N-3-hydroxypropyl-3-nitroaniline, N-3-hydroxypropyl-3-cyanoaniline, N-3-hydroxypropyl-3-acetylaniline, N-3-hydroxypropyl-3-ethoxycarbonylaniline, N-3-hydroxypropyl-3-trifluoromethylaniline, N-3-hydroxypropyl-2,5-dichloroaniline, N-3-hydroxypropyl-3,4-dichloroaniline, N-3-hydroxypropyl-3,5-dichloroaniline, N-3-hydroxypropyl-3,5-xylidine, N-3-hydroxypropyl-3,4-dimethoxyaniline, N-3-hydroxypropyl-3-chloro-4-trifluoromethylaniline, N-3-hydroxypropyl-3,5-bistrifluoromethylaniline, N-3-hydroxypropyl-2,4,5-trichloroaniline, N-3-hydroxypropyl-3,5-dimethoxyaniline, N-3-hydroxypropylaniline, N-3-hydroxypropyl-α-naphthylamine, N-3-hydroxypropyl-2-chloroaniline, N-3-hydroxypropyl-4-chloroaniline, N-3-hydroxypropyl-2-toluidine, N-3-hydroxypropyl-4-toluidine, N-3-hydroxypropyl-2-methoxyaniline, N-3-hydroxypropyl-4-methoxyaniline, N-3-hydroxypropyl-2-trifluoromethylaniline, N-3-hydroxypropyl-4-trifluoromethylaniline, N-3-hydroxypropyl-4-isopropylaniline, N-3-hydroxypropyl-2,6-xylidine and N-3-hydroxypropyl-3,4-xylidine.

Specific examples of the isocyanates of the general formula (III), which are the starting materials both in process variant (a) and in process variant (b), include phenyl isocyanate, α-naphthyl isocyanate, 2-chlorophenyl isocyanate, 3-chlorophenyl isocyanate, 4-chlorophenyl isocyanate, 2-tolyl isocyanate, 3-tolyl isocyanate, 4-tolyl isocyanate, 2-methoxyphenyl isocyanate, 3-methoxyphenyl isocyanate, 4-methoxyphenyl isocyanate, 3-nitrophenyl isocyanate, 2-trifluoromethylphenyl isocyanate, 3-trifluoromethylphenyl isocyanate, 4-trifluoromethylphenyl isocyanate, 4-isopropylphenyl isocyanate, 3,5-dichlorophenyl isocyanate, 2,6-xylyl isocyanate, 3,4-xylyl isocyanate, 3-chloro-4-trifluoromethylphenyl isocyanate, 2,4,5-trichlorophenyl isocyanate, 3-fluorophenyl isocyanate, 3-bromophenyl isocyanate, 3-isopropoxyphenyl isocyanate, 3-phenoxyphenyl isocyanate, 3-cyanophenyl isocyanate, 3-acetylphenyl isocyanate, 3-ethoxycarbonylphenyl isocyanate, 2,5-dichlorophenyl isocyanate, 3,4-dichlorophenyl isocyanate, 3,5-xylyl isocyanate, 3,4-dimethoxyphenyl isocyanate, 3,5-bistrifluoromethyl isocyanate and 3,5-dimethoxyphenyl isocyanate.

Examples of the halogenating agents to be used in process variant (a) include thionyl chloride, phosphorus trichloride, phosphorus tribromide and hydrochloric acid.

Examples of the alkali metal hydroxides to be used in the process variants (a) and (b) include sodium hydroxide, potassium hydroxide and lithium hydroxide.

Specific examples of the compounds of the general formula (IV), used as starting materials in process variant (b), include N-3-chloropropyl-3-fluoroaniline, N-3-chloropropyl-3-chloroaniline, N-3-chloropropyl-3-bromoaniline, N-3-chloropropyl-3-toluidine, N-3-chlorophenyl-3-methoxyaniline, N-3-chloropropyl-3-isopropoxyaniline, N-3-chloropropyl-3-phenoxyaniline, N-3-chloropropyl-3-nitroaniline, N-3-chloropropyl-3-cyanoaniline, N-3-chloropropyl-3-acetylaniline, N-3-chloropropyl-3-ethoxycarbonylaniline, N-3-chloropropyl-3-trifluoromethylaniline, N-3-chloropropyl-2,5-dichloroaniline, N-3-chloropropyl-3,4-dichloroaniline, N-3-chloropropyl-3,5-dichloroaniline, N-3-chloropropyl-3,5-xylidine, N-3-chloropropyl-3,4-dimethoxyaniline, N-3-chloropropyl-3-chloro-4-trifluoromethylaniline, N-3-chloropropyl-3,5-bistrifluoromethylaniline, N-3-chloropropyl-2,4,5-trichloroaniline, N-3-chloropropyl-3,5-dimethoxyaniline, N-3-chloropropylaniline, N-3-chloropropyl-α-naphthylaniline, N-3-chloropropyl-2-chloroaniline, N-3-chloropropyl-4-chloroaniline, N-3-chloropropyl-2-toluidine, N-3-chloropropyl-4-toluidine, N-3-chloropropyl-2-methoxyaniline, N-3-chloropropyl-4-methoxyaniline, N-3-chloropropyl-2-trifluoromethylaniline, N-3-chloropropyl-4-trifluoromethylaniline, N-3-chloropropyl-4-isopropylaniline, N-3-chloropropyl-2,6-xylidine and N-3-chloropropyl-3,4-xylidine, as well as their N-3-bromopropyl analogues.

Examples of the compounds of the general formula (V), to be used as starting materials in process variant (c), include 1-(3-fluoroanilino)-3-anilinopropane, 1-(3-chloroanilino)-3-anilinopropane, 1-(3-bromoanilino)-3-anilinopropane, 1-(3-toluidino)-3-anilinopropane, 1-(3-methoxyanilino)-3-anilinopropane, 1-(3-isopropoxyanilino)-3-anilinopropane, 1-(3-phenoxyanilino)-3-anilinopropane, 1-(3-nitroanilino)-3-anilinopropane, 1-(3-cyanoanilino)-3-anilinopropane, 1-(3-acetylanilino)-3-anilinopropane, 1-(3-ethoxycarbonylanilino)-3-anilinopropane, 1-(3-trifluoromethylanilino)-3-anilinopropane, 1-(3-trifluoromethylanilino)-3-α-naphthylaminopropane, 1-(3-fluoro-anilino)-3-(3-toluidino)-propane, 1-(3-chloroanilino)-3-(2-chloroanilino)propane, 1-(3-chloroanilino)-3-(3-chloroanilino)propane, 1-(3-chloroanilino)-3-(4-chloroanilino)propane, 1-(3-chloroanilino)-3-(2-toluidino)propane, 1-(3-chloroanilino)-3-(3-toluidino)propane, 1-(3-chloroanilino)-3-(4-toluidino)propane, 1-(3-chloroanilino)-3-(2-methoxyanilino)propane, 1-(3-chloroanilino)-3-(3-methoxyanilino)propane, 1-(3-chloroanilino)-3-(4-methoxyanilino)propane, 1-(3-chloroanilino)-3-(3-nitroanilino)propane, 1-(3-chloroanilino)-3-(2-trifluoromethylanilino)propane, 1-(3-chloroanilino)-3-(3-trifluoromethylanilino)propane, 1-(3-chloroanilino)-3-(4-trifluoromethylanilino)propane, 1-(3-bromoanilino)-3-(3-trifluoromethylanilino)propane, 1-(3-toluidino)-3-(2-toluidino)propane, 1,3-bis(3-toluidino)propane, 1-(3-toluidino)-3-(4-toluidino)propane, 1,3-bis(3-methoxyanilino)propane, 1-(3-methoxyanilino)-3-(3-trifluoromethylanilino)-propane, 1-(3-nitroanilino)-3-(2-toluidino)propane, 1-(3-cyanoanilino)-3-(3-trifluoromethylanilino)propane, 1-(3-trifluoromethylanilino)-3-(2-chloroanilino)propane, 1-(3-trifluoromethylanilino)-3-(4-chloroanilino)propane, 1-(3-trifluoromethylanilino)-3-(2-toluidino)propane, 1-(3-trifluoromethylanilino)-3-(3-toluidino)propane, 1-(3-trifluoromethylanilino)-3-(4-isopropylanilino)propane, 1-(3-trifluoromethylanilino)-3-(2-methoxyanilino)propane, 1-(3-trifluoromethylanilino)-3-(4-methoxyanilino)propane, 1,3-bis(3-trifluoromethylanilino)propane, 1-(2,5-dichloroanilino)-3-anilinopropane, 1-(3,4-dichloroanilino)-3-anilinopropane, 1-(3,5-dichloroanilino)-3-anilinopropane, 1-(3,5-xylidino)-3-anilinopropane, 1-(3,4-dimethoxyanilino)-3-anilinopropane, 1-(3-chloro-4-trifluoromethylanilino)-3-anilinopropane, 1-(3,5-bistrifluoromethylanilino)-3-anilinopropane, 1-(3-chloroanilino)-3-(3,5-dichloroanilino)propane, 1-(3-trifluoromethylanilino)-3-(3,5-dichloroanilino)propane, 1-(3-trifluoromethylanilino)-3-(2,6-xylidino)propane, 1-(3-trifluoromethylanilino)-3-(3,4-xylidino)propane, 1-(3-trifluoromethylanilino)-3-(3-chloro-4-trifluoromethylanilino)propane, 1-(3,4-dichloroanilino)-3-(2-toluidino)propane, 1-(2,4,5-trichloroanilino)-3-anilinopropane, 1-(3-trifluoromethylanilino)-3-(2,4,5-trichloroanilino)propane, 1-(3,5-dimethoxyanilino)-3-anilinopropane, 1-(3-phenoxyanilino)-3-(3-trifluoromethylanilino)propane, 1-(3,5-dichloroanilino)-3-(2-methoxyanilino)propane and 1-α-naphthylamino-3-anilinopropane.

In process varients (a) and (b) the reaction sequence can be carried out continuously, that is to say without isolation of the intermediates.

Process variants (a), (b) and (c) are preferably carried out using a solvent or a diluent. For this purpose, any inert solvent or diluent can be used.

Examples of such solvents or diluents include water; aliphatic, alicyclic and aromatic hydrocarbons (optionally chlorinated), such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, di-isopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethyl formamide and dimethyl acetamide; sulfones and sulfoxides such as dimethyl sulfoxide and sulfolane; and bases such as pyridine.

Of course, a mixture of solvents and/or diluents could be used.

Process variant (b) can be effected in the presence of a catalyst, for example a quaternary ammonium salt, such as tetrabutylammonium bromide.

The reaction in process variant (c) may be carried out in the presence of an acid-binding agent. Examples of such acid-binding agents are alkali metal hydroxides, carbonates, bicarbonates and alcoholates and tertiary amines such as triethylamines, diethylaniline and pyridine, which compounds find general use as acid acceptors.

Process variants (a), (b) and (c) can be carried out at a temperature within a broad range. Generally, the reaction is carried out at a temperature between −20° C. and the boiling point of the mixture, preferably at a temperature between 0° and 100° C. Preferably, the reaction, in any of the variants, is carried out at atmospheric pressure, although it may be effected under elevated or reduced pressures.

The active compounds according to the invention influence plant growth and can therefore be used as defoliants, desiccants, agents for destroying broad-leaved plants, germination inhibitors and, especially, as weedkillers. By "weeds" in the broadest sense that are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The present compounds are very effective when used to combat weeds occurring in paddy fields and show substantially no phytotoxicity to the rice plants being cultivated. The compounds can be used before, during and after the emergence of the weeds. They can be applied for example to the soil and/or to the stems and leaves of the weeds. As examples of paddy-field weeds there may be mentioned *Rotala indica, Lindernia procumbens, Ludwiga prostrata, Potamogeton distinctus, Elatine triandra, Echinochloa crus-galli, Monochoria vaginalis, Eleocharis acicularis, Eleocharis kuroguwai, Cyperus difformis, Cyperus serotinus, Sagittaria pygmaea, Alisma canaliculatum* and *Scirpus juncoides*.

The active compounds can be converted into the customary formulations, such as solutions, emulsions, wettable powders, suspensions, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or form-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.01 to 100 percent by weight of active compound, preferably from 0.05 to 95 percent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They may be used in the customary manner, for example by watering, spraying, atomizing, scattering or dusting.

The amount of active compound in the ready-to-use preparations can vary widely according to circumstance. However, it is in general from 0.01 to 95 percent, preferably from 0.05 to 60 percent by weight.

The compounds can also be used in the ultra-low-volume method, wherein the preparation used can contain up to 100% of the active ingredient.

The active compounds can be applied after emergence of the plants or before emergence of the plants, that is to say by the pre-emergence method. They can also be incorporated into the soil before sowing.

The amount of active compound used can vary within a substantial range. It depends essentially on the nature of the desired effect. In general, the amounts used are between 0.1 and 5 kg of active compound per hectare, preferably between 0.2 and 4 kg/ha.

The present invention also provides a herbicidal composition containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The following examples serve to illustrate the invention further:

PREPARATIVE EXAMPLES

EXAMPLE 1

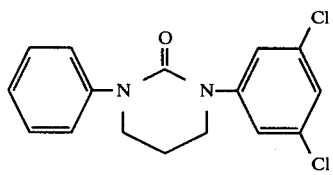
(1)

15.1 g of N-3-hydroxypropylaniline were dissolved in 80 ml of chloroform, and a solution of 18.8 g of 3,5-dichlorophenyl isocyanate in 30 ml of chloroform was added thereto at a temperature of 30° C. or below. The reaction was mildly exothermic, and cooling was applied as necessary. After stirring at room temperature for a while, the mixture was refluxed for 0.5 hours to complete the urea formation reaction. Then, the mixture was cooled to a temperature of 10° C. or below and, after adding a few drops of pyridine thereto, 14.3 g of thionyl chloride were added at a temperature of 10° C. or below. The mixture was stirred at room temperature for a while and, when the evolution of gas had ceased, it was further heated and refluxed for an hour. Removal of excess thionyl chloride and chloroform under reduced pressure gave the crude chloride as a residue. This crude chloride was dissolved in 50 ml of ethanol, to which was added a solution of 11.2 g of potassium hydroxide in 40 ml of ethanol and the mixture was refluxed for 2 hours while thoroughly stirring. After the reaction, most of the ethanol was removed under reduced pressure and the residue was poured into water, whereupon crystals of the crude product were precipitated. Recrystallization from methanol gave 27.3 g of the desired product, 1-(3,5-dichlorophenyl)-3-phenyl-tetrahydro-2-pyrimidinone; m.p. 128°–129° C.

EXAMPLE 2

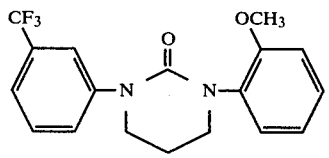
(2)

23.8 g of N-3-chloropropyl-3-trifluoromethylaniline were dissolved in 150 ml of toluene, 14.9 g of 2-methoxyphenyl isocyanate were added thereto, and the mixture was heated at 50°–60° C. with stirring for 3 hours. Then, the mixture was cooled to 30° C., a catalytic amount of tetrabutylammonium bromide was added, and with vigorous stirring, 25 g of a 50% aqueous sodium hydroxide solution were added. After addition, the mixture was heated with stirring at 50° C. and, after allowing it to cool to room temperature, the aqueous layer was separated, and the toluene layer was washed with water. Removal of toluene under reduced pressure gave 26.3 g of the desired product 1-(2-methoxyphenyl)-3-(3-trifluoromethyl)-tetrahydro-2-pyrimidinone, as colorless crystals; m.p. 97°–98° C.

EXAMPLE 3

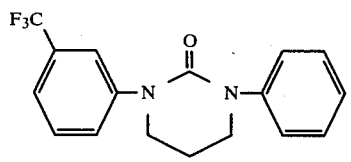
(3)

29.4 g of 1-(3-trifluoromethylanilino)-3-anilinopropane were dissolved in 150 ml of toluene, and 22.2 g of triethylamine were added thereto. This solution was cooled to 0° C., and a solution of 10.9 g of trichloromethyl chloroformate in 20 ml of toluene was added dropwise at 0°–5° C. After this addition, the mixture was stirred at room temperature for 3 hours. The mixture was then washed with a 1% hydrochloric acid solution, with a 1% aqueous sodium hydroxide solution and then with water. The mixture was subsequently dried and toluene was removed under reduced pressure to obtain 25.0 g of the desired product, 1-phenyl-3-(3-trifluoromethylphenyl)-tetrahydro-2-pyrimidinone; m.p. 101°–103° C.

The compounds of this invention given below in Table 1 were obtained by methods analogous to those described in the above examples; Ph represents phenyl ($-C_6H_5$).

TABLE 1

Ar—N(C=O)N—Ar (I)

| Compound No. | Ar | Ar | m.p. (°C.) |
|---|---|---|---|
| 4 | 3-F—Ph | Ph | 116–118.5 |
| 5 | 3-Cl—Ph | Ph | 116–117 |
| 6 | 3-Br—Ph | Ph | 117–118 |
| 7 | 3-CH$_3$—Ph | Ph | 78–79 |
| 8 | 3-CH$_3$O—Ph | Ph | 110–111 |
| 9 | 3-iso-C$_3$H$_7$—Ph | Ph | 92–93.5 |
| 10 | 3-Ph—O—Ph | Ph | 101–104 |
| 11 | 3-NO$_2$—Ph | Ph | 131.5–132.5 |
| 12 | 3-NC—Ph | Ph | 133–135 |
| 13 | 3-CH$_3$C(=O)—Ph | Ph | 118–121 |
| 14 | 3-C$_2$H$_5$OC(=O)—Ph | Ph | 111–112 |
| 15 | 3-CF$_3$—Ph | 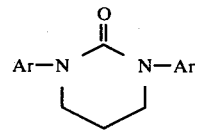 | 118.5–120 |
| 16 | 3-F—Ph | 3-CH$_3$—Ph | 115–117 |
| 17 | 3-Cl—Ph | 2-Cl—Ph | 122–123.5 |
| 18 | 3-Cl—Ph | 3-Cl—Ph | 170.5–171.5 |
| 19 | 3-Cl—Ph | 4-Cl—Ph | 162.5–163.5 |
| 20 | 3-Cl—Ph | 2-CH$_3$—Ph | 101–102 |
| 21 | 3-Cl—Ph | 3-CH$_3$—Ph | 145–147.5 |
| 22 | 3-Cl—Ph | 4-CH$_3$—Ph | 167–169.5 |
| 23 | 3-Cl—Ph | 2-CH$_3$O—Ph | 117–118 |
| 24 | 3-Cl—Ph | 3-CH$_3$O—Ph | 99–100 |
| 25 | 3-Cl—Ph | 4-CH$_3$O—Ph | 157–158 |
| 26 | 3-Cl—Ph | 3-NO$_2$—Ph | 137–138.5 |
| 27 | 3-Cl—Ph | 2-CF$_3$—Ph | 113–114 |
| 28 | 3-Cl—Ph | 3-CF$_3$—Ph | 143.5–145 |

TABLE 1-continued $$Ar-N \overset{\overset{O}{\|}}{\underset{\underset{\phantom{x}}{\phantom{x}}}{C}} N-Ar \qquad (I)$$

| Compound No. | Ar | | m.p. (°C.) |
|---|---|---|---|
| 29 | 3-Cl—Ph | 4-CF$_3$—Ph | 125–126 |
| 30 | 3-Br—Ph | 3-CF$_3$—Ph | 154–155 |
| 31 | 3-CH$_3$—Ph | 2-CH$_3$—Ph | 99.5–100.5 |
| 32 | 3-CH$_3$—Ph | 3-CH$_3$—Ph | 117–118.5 |
| 33 | 3-CH$_3$—Ph | 4-CH$_3$—Ph | 115.5–116.5 |
| 34 | 3-CH$_3$O—Ph | 3-CH$_3$O—Ph | 90–93 |
| 35 | 3-CH$_3$O—Ph | 3-CF$_3$—Ph | 123–124.5 |
| 36 | 3-NO$_2$—Ph | 2-CH$_3$—Ph | 127–130 |
| 37 | 3-NC—Ph | 3-CF$_3$—Ph | 140.5–143 |
| 38 | 3-CF$_3$—Ph | 2-Cl—Ph | 118–121 |
| 39 | 3-CF$_3$—Ph | 4-Cl—Ph | 126.5–127.5 |
| 40 | 3-CF$_3$—Ph | 3-CH$_3$—Ph | 119–120 |
| 41 | 3-CF$_3$—Ph | 3-CH$_3$—Ph | 157–160 |
| 42 | 3-CF$_3$—Ph | 4-iso-C$_3$H$_7$—Ph | 133–134 |
| 43 | 3-CF$_3$—Ph | 4-CH$_3$O—Ph | 128–130 |
| 44 | 3-CF$_3$—Ph | 3-CF$_3$—Ph | 143–146 |
| 45 | 2,5-Cl$_2$—Ph | Ph | 127–128 |
| 46 | 3,4-Cl$_2$—Ph | Ph | 132–133 |
| 47 | 3,5-(CH$_3$)$_2$—Ph | Ph | 115–117 |
| 48 | 3,4-(CH$_3$O)$_2$—Ph | Ph | 120–122 |
| 49 | 3-Cl,4-CF$_3$—Ph | Ph | 139–140.5 |
| 50 | 3,5-(CF$_3$)$_2$—Ph | Ph | 176–178 |
| 51 | 3-Cl—Ph | 3,5-Cl$_2$—Ph | 117–118 |
| 52 | 3-CF$_3$—Ph | 3,5-Cl$_2$—Ph | 94–95.5 |
| 53 | 3-CF$_3$—Ph | 2,6-(CH$_3$)$_2$—Ph | 113–114 |
| 54 | 3-CF$_3$—Ph | 3,4-(CH$_3$)$_2$—Ph | 165–166.5 |
| 55 | 3-CF$_3$—Ph | 3-Cl,4-CF$_3$—Ph | 124–125 |
| 56 | 3,4-Cl$_2$—Ph | 2-CH$_3$—Ph | 146–147.5 |
| 57 | 2,4,5-Cl$_3$—Ph | Ph | 174–175 |
| 58 | 3-CF$_3$—Ph | 2,4,5-Cl$_3$—Ph | 147–150 |
| 59 | 3,5-(CH$_3$O)$_2$—Ph | Ph | 95.5–96.5 |
| 60 | 3-Ph—O—Ph | 3-CF$_3$—Ph | 101–102 |
| 61 | 3,5-Cl$_2$—Ph | 2-CH$_3$O—Ph | 160–161 |
| 62 | naphthyl | Ph | 177–178 |

Compositions according to this invention are illustrated in the following examples.

In these examples, the compounds according to the present invention are each identified by the number (given in brackets) from Examples 1 to 3 and Table 1 hereinabove.

EXAMPLE 4

Fifteen parts of compound (6), 80 parts of a 1:5 mixture of powdered diatomaceous earth and powdered clay, 2 parts of sodium alkylbenzenesulfonate and 3 parts of a sodium alkylnaphthalenesulfonate/formaldehyde condensate were ground and mixed to form a wettable powder. The wettable powder was diluted with water before use.

EXAMPLE 5

Thirty parts of compound (10), 55 parts of xylene, 8 parts of polyoxyethylene alkylphenyl ether and 7 parts of calcium alkylbenzenesulfonate were mixed with stirring to form an emulsifiable concentrate. The emulsifiable concentrate was diluted with water before use.

EXAMPLE 6

Two parts of compound (25) and 98 parts of powdered clay were pulverized and mixed to form a dusting agent.

EXAMPLE 7

1.5 parts of compound (40), 0.5 part of isopropyl hydrogen phosphate (PAP) and 98 parts of powdered clay were ground and mixed to form a dusting agent.

EXAMPLE 8

25 parts of water were added to a mixture of 10 parts of compound (1), 30 parts of bentonite (montmorillonite), 58 parts of talc and 2 parts of lignin sulfonate, and they were well kneaded. The mixture was formed into granules having a size of 10 to 40 mesh by means of an extrusion-type granulator, and dried at 40° to 50° C. to form granules.

EXAMPLE 9

A rotary mixer was charged with 95 parts of clay mineral particles having a particle size distribution in the range of 0.2 to 2 mm, and, while rotating the mixer, 5 parts of compound (2) dissolved in an organic solvent were sprayed uniformly onto the clay mineral particles. The particles were then dried at 40° to 50° C. to form granules.

The herbicidal activity of the compounds of this invention is illustrated by the following biotest examples.

In these examples, the compounds according to the present invention are each identified by the number (given in brackets) from Examples 1 to 3 and Table 1 hereinabove.

The known comparison compound is identified as follows:

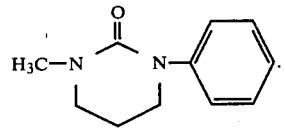

(Z)

This compound is disclosed Chemical Abstracts, volume 57, 9860a, 1968.

EXAMPLE 10

Test against aquatic paddy-field weeds by treating the soil and stems and leaves under irrigation conditions (pot test)

Preparation of an active compound

| Carrier: | 5 parts by weight of acetone |
|---|---|
| Emulsifier: | 1 part by weight of benzyloxy polyglycol ether |

A preparation of the active compound was obtained as an emulsifiable concentrate by mixing 1 part by weight of the active compound with the aforesaid amounts of the carrier and emulsifier. A predetermined amount of the preparation was obtained by dilution with water.

Test procedure

Wagner pots (1/5,000 are) were filled with paddy-field soil, and two rice seedlings (variety: Kinmaze)

were transplanted in each pot. Seeds of *Echinochloa crus-galli*, *Cyperus iria*, *Monochoria vaginalis*, *Scirpus juncoides* and certain broad-leaved weeds, small pieces of *Eleocharis acicularis* and tubers of *Cyperus serotinus* and *Sagittaria pygmaea* were put into the pots, and the pots were maintained in a wet condition. When the *Echinochloa crus-galli* had grown to approximately the two-leaf stage (about 7 to 9 days after the sowing), the pots were filled with water to a depth of about 6 cm, and a predetermined amount of the active compound in the form of an emulsion was applied by means of a pipette. After the treatment, the water was allowed to leak from the pots at a rate of 2 to 3 cm per day for two days. Then, the depth of water in the pots was maintained at about 3 cm, and four weeks after the treatment with the active compound, the herbicidal effect and the degree of phytotoxicity were evaluated on a scale of from 0 to 5 in accordance with the following standards.

The herbicidal effect was evaluated as follows in comparison with an untreated control.

| Rating | Weed-kill ratio based on the control |
|---|---|
| 5: | at least 95% (withered) |
| 4: | at least 80% but less than 95% |
| 3: | at least 50% but less than 80% |
| 2: | at least 30% but less than 50% |
| 1: | at least 10% but less than 30% |
| 0: | less than 10% (not effective) |

The phytotoxicity towards the rice plants was evaluated as follows in comparison with the untreated.

| Rating | Phytotoxicity rate in comparison with the control |
|---|---|
| 5: | at least 90% (fatal damage) |
| 4: | at least 50% but less than 90% |
| 3: | at least 30% but less than 50% |
| 2: | at least 10% but less than 30% |
| 1: | more than 0 but less than 10% |
| 0: | 0% (no phytotoxicity) |

The test results are shown in Table 2, in which the symbols A to H represent the following weeds:

A: *Echinochloa crus-galli* Beauv. var
B: *Eleocharis acicularis* L.
C: *Cyperus iria* L.
D: *Scirpus juncoides* Roxburgh var.
E: *Monochoria vaginalis* Presl.
F: broad-leaved weeds (including *Lindernia procumbens* Philcox, *Rotala indica* Koehne, *Elatine triandra* Schk).
G: *Cyperus serotinus* Rottboel
H: *Sagittaria pygmaea* Miq.

TABLE 2

| Compound | Amount of the active ingredient kg/ha | Herbicidal effect |||||||| Phytotoxicity |
|---|---|---|---|---|---|---|---|---|---|---|
| | | A | B | C | D | E | F | G | H | |
| (1) | 2.0 | 5 | 5 | 5 | 5 | 5 | 5 | 5 | 5 | 0 |
| (2) | " | 5 | 5 | 5 | 5 | 5 | 5 | 5 | 5 | 0 |
| (3) | " | 5 | 5 | 5 | 5 | 5 | 5 | 5 | 5 | 0 |
| (4) | " | 5 | 5 | 5 | 5 | 5 | 5 | 5 | 5 | 0 |
| (5) | " | 5 | 5 | 5 | 5 | 5 | 5 | 5 | 5 | 0 |
| (6) | " | 5 | 5 | 5 | 5 | 5 | 5 | 5 | 5 | 0 |
| (7) | " | 5 | 5 | 5 | 5 | 5 | 5 | 5 | 5 | 0 |
| (8) | " | 5 | 5 | 5 | 5 | 5 | 5 | 5 | 5 | 0 |
| (9) | " | 5 | 5 | 5 | 5 | 5 | 5 | 5 | 5 | 0 |

TABLE 2-continued

| Compound | Amount of the active ingredient kg/ha | Herbicidal effect |||||||| Phytotoxicity |
|---|---|---|---|---|---|---|---|---|---|---|
| | | A | B | C | D | E | F | G | H | |
| (10) | " | 5 | 5 | 5 | 5 | 5 | 5 | 5 | 5 | 0 |
| (12) | " | 5 | 5 | 5 | 5 | 5 | 5 | 5 | 5 | 0 |
| (15) | " | 5 | 5 | 5 | 5 | 5 | 5 | 5 | 5 | 0 |
| (16) | " | 5 | 5 | 5 | 5 | 5 | 5 | 5 | 5 | 0 |
| (17) | " | 5 | 5 | 5 | 5 | 5 | 5 | 5 | 5 | 0 |
| (18) | " | 5 | 5 | 5 | 5 | 5 | 5 | 5 | 5 | 0 |
| (19) | " | 5 | 5 | 5 | 5 | 5 | 5 | 5 | 5 | 0 |
| (20) | " | 5 | 5 | 5 | 5 | 5 | 5 | 5 | 5 | 0 |
| (21) | " | 5 | 5 | 5 | 5 | 5 | 5 | 5 | 5 | 0 |
| (22) | " | 5 | 5 | 5 | 5 | 5 | 5 | 5 | 5 | 0 |
| (23) | " | 5 | 5 | 5 | 5 | 5 | 5 | 5 | 5 | 0 |
| (24) | " | 5 | 5 | 5 | 5 | 5 | 5 | 5 | 5 | 0 |
| (25) | " | 5 | 5 | 5 | 5 | 5 | 5 | 5 | 5 | 0 |
| (26) | " | 5 | 5 | 5 | 5 | 5 | 5 | 5 | 5 | 0 |
| (27) | " | 5 | 5 | 5 | 5 | 5 | 5 | 5 | 5 | 0 |
| (28) | " | 5 | 5 | 5 | 5 | 5 | 5 | 5 | 5 | 0 |
| (30) | " | 5 | 5 | 5 | 5 | 5 | 5 | 5 | 5 | 0 |
| (31) | " | 5 | 5 | 5 | 5 | 5 | 5 | 5 | 5 | 0 |
| (32) | " | 5 | 5 | 5 | 5 | 5 | 5 | 5 | 5 | 0 |
| (33) | " | 5 | 5 | 5 | 5 | 5 | 5 | 5 | 5 | 0 |
| (34) | " | 5 | 5 | 5 | 5 | 5 | 5 | 5 | 5 | 0 |
| (35) | " | 5 | 5 | 5 | 5 | 5 | 5 | 5 | 5 | 0 |
| (36) | " | 5 | 5 | 5 | 5 | 5 | 5 | 5 | 5 | 0 |
| (37) | " | 5 | 5 | 5 | 5 | 5 | 5 | 5 | 5 | 0 |
| (38) | " | 5 | 5 | 5 | 5 | 5 | 5 | 5 | 5 | 0 |
| (39) | " | 5 | 5 | 5 | 5 | 5 | 5 | 5 | 5 | 0 |
| (40) | " | 5 | 5 | 5 | 5 | 5 | 5 | 5 | 5 | 0 |
| (41) | " | 5 | 5 | 5 | 5 | 5 | 5 | 5 | 5 | 0 |
| (43) | " | 5 | 5 | 5 | 5 | 5 | 5 | 5 | 5 | 0 |
| (44) | " | 5 | 5 | 5 | 5 | 5 | 5 | 5 | 5 | 0 |
| (45) | " | 5 | 5 | 5 | 5 | 5 | 5 | 5 | 5 | 0 |
| (46) | " | 5 | 5 | 5 | 5 | 5 | 5 | 5 | 5 | 0 |
| (47) | " | 5 | 5 | 5 | 5 | 5 | 5 | 5 | 5 | 0 |
| (50) | " | 5 | 5 | 5 | 5 | 5 | 5 | 5 | 5 | 0 |
| (51) | " | 5 | 5 | 5 | 5 | 5 | 5 | 5 | 5 | 0 |
| (52) | " | 5 | 5 | 5 | 5 | 5 | 5 | 5 | 5 | 0 |
| (53) | " | 5 | 5 | 5 | 5 | 5 | 5 | 5 | 5 | 0 |
| (54) | " | 5 | 5 | 5 | 5 | 5 | 5 | 5 | 5 | 0 |
| (55) | " | 5 | 5 | 5 | 5 | 5 | 5 | 5 | 5 | 0 |
| (56) | " | 5 | 5 | 5 | 5 | 5 | 5 | 5 | 5 | 0 |
| (57) | " | 5 | 5 | 5 | 5 | 5 | 5 | 5 | 5 | 0 |
| (60) | " | 5 | 5 | 5 | 5 | 5 | 5 | 5 | 5 | 0 |
| (62) | " | 5 | 5 | 5 | 5 | 5 | 5 | 5 | 5 | 0 |
| (Z) | 4.0 | 1 | 0 | 1 | 0 | 1 | 2 | 0 | 2 | 0 |

Furthermore, in tests similar to the above, it was confirmed that the compounds (11), (13), (14), (29), (42), (48), (49), (58), (59) and (61) have an excellent herbicidal activity (100% weed control at a dosage of the active ingredient of 2 kg/ha) without exhibiting any phytotoxicity towards rice plants.

It will be understood that the specification and examples are illustrative but not limitative of the present invention and that other embodiments within the spirit and scope of the invention will suggest themselves to those skilled in the art.

We claim:

1. A substituted tetrahydropyrimidinone of the formula

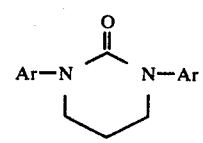

in which
Ar each independently is an α-naphthyl group or a group of the formula,

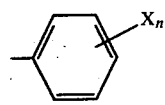

X is halogen, lower alkyl, lower alkoxy, nitro, cyano, lower alkylcarbonyl, lower alkoxycarbonyl, trifluoromethyl or phenoxy, and n is 0, 1, 2 or 3.

2. A compound according to claim 1, in which

X in at least one instance is fluorine, chlorine, bromine, methyl, isopropyl, methoxy, isopropoxy, nitro, cyano, acetyl, ethoxycarbonyl, trifluoromethyl or phenoxy.

3. A compound according to claim 1, in which at least one Ar is

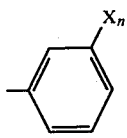

4. A compound according to claim 1, wherein such compound is 1-(2-methoxyphenyl)-3-(trifluoromethylphenyl)-tetrahydro-2-pyrimidinone of the formula

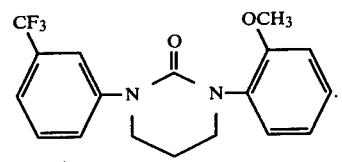

5. A compound according to claim 1, wherein such compound is 1-(3,5-dichlorophenyl)-3-phenyltetrahydro-2-pyrimidinone of the formula

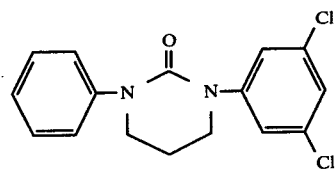

6. A herbicidal composition comprising a herbicidally effective amount of a compound according to claim 1 in admixture with a diluent.

7. A method of combating weeds which comprises applying to the weeds, or to a habitat thereof, a herbicidally effective amount of a compound according to claim 1.

8. The method according to claim 7, wherein such compound is
1-(2-methoxyphenyl)-3-(trifluoromethylphenyl)-tetrahydro-2-pyrimidinone or
1-(3,5-dichlorophenyl)-3-phenyltetrahydro-2-pyrimidinone.

* * * * *